(12) United States Patent
Atalla (10) Patent No.: US 8,617,851 B2
(45) Date of Patent: Dec. 31, 2013

(54) HIGHLY DISORDERED CELLULOSE

(75) Inventor: Rajai H. Atalla, Verona, WI (US)

(73) Assignee: Cellulose Sciences International, Inc., Verona, WI (US)

( * ) Notice: Subject to any disclaimer, the term of this patent is extended or adjusted under 35 U.S.C. 154(b) by 51 days.

(21) Appl. No.: 12/935,447

(22) PCT Filed: Apr. 3, 2009

(86) PCT No.: PCT/US2009/039445

§ 371 (c)(1),
(2), (4) Date: Dec. 28, 2010

(87) PCT Pub. No.: WO2009/124240

PCT Pub. Date: Oct. 8, 2009

(65) Prior Publication Data

US 2011/0091940 A1    Apr. 21, 2011

Related U.S. Application Data (60) Provisional application No. 61/042,133, filed on Apr. 3, 2008.

(51) Int. Cl.
*C12P 7/10* (2006.01)

(52) U.S. Cl.
USPC ............................ 435/105; 435/165; 435/166

(58) Field of Classification Search
None
See application file for complete search history.

(56) References Cited

U.S. PATENT DOCUMENTS

| | | | | |
|---|---|---|---|---|
| 4,395,543 | A * | 7/1983 | Wang et al. ..................... | 536/56 |
| 5,858,021 | A | 1/1999 | Sun et al. | |
| 2008/0060774 | A1 | 3/2008 | Zuraw et al. | |

FOREIGN PATENT DOCUMENTS

| WO | WO 2007111605 A1 * | 10/2007 | ............... C13K 1/02 |
|---|---|---|---|
| WO | 2009/124240 | 10/2009 | |
| WO | 2012/027767 | 3/2012 | |
| WO | 2012/037250 | 3/2012 | |
| WO | 2012/109651 | 8/2012 | |

OTHER PUBLICATIONS

Bandura et al., The ionization constant of water over wide ranges of temperature and density, 2006, Journal of Physical and Chemical Reference Data 35(1): 15-30.*
International Search Report and Written Opinion for Application No. PCT/US2011/51592 dated Mar. 28, 2012 (18 pages).
Agarwal, U.P. et al., "Cellulose I crystallinity determination using FT-Raman spectroscopy: univariate and multivariate methods," Cellulose (2010) 17:721-733.
Park, S. et al., "Cellulose crystallinity index: measurement techniques and their impact on interpreting cellulase performance," Biotechnol. Biofuels (2010) 3:10.
Atalla et al., "An innovative new technology to reduce recalcitrance of cellulose and make it competitive with corn as a biomass feedstock," (2009) 1-6, retrieved from the Internet: URL:celscint.com/uploads/CSI_Technology.pdf, retrieved on Aug. 24, 2009; XP-002542665.
European Patent Office Action for Application No. 09728575.3 dated Feb. 25, 2011 (6 pages).
International Search Report and Written Opinion for Application No. PCT/US2012/024871 dated Aug. 2, 2012 (11 pages).

* cited by examiner

*Primary Examiner* — Jon P Weber
*Assistant Examiner* — Robert Yamasaki
(74) *Attorney, Agent, or Firm* — Michael Best & Friedrich LLP (57) ABSTRACT

Disclosed are methods and systems for treating cellulose to make it more accessible for enzymatic or chemical modification. The invention includes treating cellulose with an alkali in an alcohol/water co-solvent system. The treatment decrystallizes or deaggregates the cellulosic material. The methods and systems increase the efficiency of enzymatic or chemical modifications of cellulose for use as biofuels or cellulose derivatives.

17 Claims, 7 Drawing Sheets

X-ray diffractograms of bleached kraft pulp before and after decrystallization treatment.

X-ray diffractograms of cellulose isolated from southern pine. (C) control pulped at 60°C, (A) Annealed heated up to 150°C in water.

FIG. 3

Width at half-height of samples annealed at different temperatures

HIGHLY DISORDERED CELLULOSE

CROSS-REFERENCE TO RELATED APPLICATIONS

This application is a national stage filing under 35 U.S.C. 371 of International Application No. PCT/US2009/039445, filed on Apr. 3, 2009, which claims the benefit under 35 U.S.C. §119(e) of U.S. Provisional Application No. 61/042,133, filed on Apr. 3, 2008, the complete disclosures of which are incorporated herein by reference in their entireties.

STATEMENT REGARDING FEDERALLY SPONSORED RESEARCH OR DEVELOPMENT

Not Applicable.

INTRODUCTION

Cellulose is the most abundant of all naturally occurring polymers. Chemically, it is a polysaccharide composed of anhydroglucose units (β-D glucopyranose rings) joined by an oxygen linkage (β-1,4-glycosidic linkage), and has the empirical formula $(C_6H_{10}O_5)_n$. Cellulose is the most characteristic component of plant cell walls as it forms much of the structural framework of the cell wall. It has a linear chain structure that forms crystalline nanofibrils in which many parallel β-1,4-glucan strands associate side by side to form nano-scale microfibrils (2-20 nm diameter and 100-40,000 nm long) that have great tensile strength and chemical stability, and are very resistant to breakdown, e.g., enzymatic, chemical and mechanical degradation. Cellulose is insoluble in water and simple organic solvents. It will swell in sodium hydroxide solutions and is soluble in Schweitzer's reagent.

Commercially, cellulose is used to make paper, plastics, and textiles. Cellulose derivatives include rayon, cellophane, thickeners used in foods and paints, and coatings. More recently, the biofuels industry has shown great interest in cellulosic feedstocks for producing biofuels, such as alcohols, e.g., ethanol or butanol, through microbiological processes, as well as hydrocarbons through chemical catalytic conversion.

The attractiveness of producing biofuels from cellulosic feedstocks, such as agricultural wastes, grasses, and forestry wastes, emanates from the availability of large amounts of these inexpensive feedstocks, and the desirability to avoid burning or landfilling cellulosic waste materials. Some cellulosic feedstocks that may be used for biofuels production specifically include (1) agricultural wastes, such as corn stover, wheat straw, barley straw, rice straw, oat straw, oat hulls, canola straw, and soybean stover; (2) grasses, such as switch grass, miscanthus, cord grass, and reed canary grass; (3) forestry wastes, such as aspen wood and sawdust; and (4) sugar processing residues, such as bagasse and beet pulp.

The conversion process of cellulosic fibers to a biofuel requires: 1) liberating cellulose and hemicellulose from lignin or increasing accessibility of cellulose and hemicellulose within the cellulosic feedstock to cellulase enzymes; and 2) depolymerizing or hydrolyzing hemicellulose and cellulose carbohydrate polymers to free sugars. To produce alcohols, the sugars are then fermented to an alcohol, e.g., ethanol, and the alcohol recovered, typically via distillation. Alternatively, the sugars can be converted to hydrocarbons through catalytic reformulation.

However, as noted above, cellulose contained in most plant matter is not readily convertible to sugars, and this step represents a major hurdle in the commercialization of processes for biofuels production. Because of the crystalline structure of cellulose, enzymatic conversion to sugars, for example, takes a considerable amount of time and requires large quantities of hydrolytic enzymes, such as cellulases. Likewise for the production of chemically-modified cellulose derivatives, cellulose must be made accessible to reactive chemical agents; this usually requires high temperature, pressures, harsh chemical conditions, and extended periods of time.

The efficient conversion of cellulose from cellulosic material into sugars was originally thought to simply involve liberating cellulose and hemicellulose from their complex with lignin. However, more recent processes focus on increasing the accessibility to cellulose within the lignocellulosic biomass followed by depolymerization or hydrolysis of cellulose carbohydrate polymers to sugars. Increasing the accessibility to cellulose is most often accomplished by pretreating the cellulosic substrate.

The goal of most pretreatment methods is to deliver a sufficient combination of mechanical and chemical action, so as to disrupt the fiber structure and improve the accessibility of the feedstock to hydrolytic enzymes, such as cellulases, which can hydrolyze cellulose. Mechanical action typically includes the use of pressure, grinding, milling, agitation, shredding, compression/expansion, or other types of mechanical action. Chemical action typically includes the use of heat (often steam), acid, and organic solvents.

Even with the most efficient of the currently known pretreatment processes, the amount of hydrolytic enzymes required to convert cellulose to sugars continues to be high and represents a significant cost in cellulosic biofuel production. Thus, the efficient conversion of cellulose from cellulosic material into sugars, and, for example, the subsequent fermentation of sugars to alcohol, such as ethanol, faces a major challenge for commercial viability. Increasing hydrolysis times to avoid higher costs of increasing enzyme dosage requires larger reactors, which, in turn, increases equipment costs. Mixing and intermittent mixing of the feedstock during hydrolysis can increase enzyme efficiency but equipment costs again increase, and increased shear forces can cause enzyme denaturation. Still other systems compromise the optimal enzyme activity and reduce the efficiency of the enzymes.

Furthermore, the difficulty with the conversion of cellulose to high value-added products extends well beyond biofuel production. As noted, cellulose derivatives include fibers and plastics, e.g., regenerated celluloses such as rayon and cellophane, cellulose esters such as acetate, butyrate, triacetate and mixed esters, cellulose nitrate, viscose, and lyocell (Tencel). Some of the cellulose crystalline domains are so tightly aggregated that chemical reagents cannot fully penetrate them, similar to lack of access for enzymes to hydrolyze them fully. The result is that the degree of substitution along the chains of cellulose in the cellulose derivatives can be quite irregular resulting in quality control problems.

BRIEF DESCRIPTION

According to the principles manifest in embodiments of the invention, methods and systems are provided which deaggregate or decrystallize cellulose so that it is more accessible for enzymatic or chemical modification, e.g., depolymerization or hydrolysis reactions. The methods and systems, in effect, enhance the conversion of cellulose-based feedstocks for use in production of biofuels and cellulose derivatives.

The methods and systems herein include treating cellulosic feedstocks with a solution of an alkali in a co-solvent system, including water and a second solvent that is polar and fully water-miscible, to form a decrystallized cellulose, and stabilizing the decrystallized cellulose by washing out the alkali to yield a decrystallized cellulose in an aqueous medium. The washing may be accomplished with a co-solvent system that is the same as in the treating step with the varying ratios of water and second solvent. Among the most effective co-solvents identified so far are alcohols. In embodiments of the invention, this process is carried out under mild conditions of temperature and pressure.

BRIEF DESCRIPTION OF THE DRAWINGS

The invention may be better understood and appreciated by reference to the detailed description of specific embodiments presented herein in conjunction with the accompanying drawings of which.

DETAILED DESCRIPTION

Methods and systems embodying the principles of the invention are provided in which cellulosic materials are decrystallized or deaggregated by treatments which include contacting a cellulosic material with an alkali in a co-solvent system that includes water and a water-miscible solvent, e.g., an alcohol or polyol. The decrystallized cellulose is more accessible for enzymatic and chemical reaction. The methods and systems in accordance with embodiments of the invention, thus, increase the efficiency of enzymatic or chemical modification of cellulose for use as biofuels or cellulose derivatives.

Before any embodiments of the invention are explained in detail, however, it is to be understood that the invention is not limited in its application to the details of construction and the arrangement of components set forth in the following description, illustrated in the following drawings or exemplified by the Examples. Such description, drawings, and Examples are not intended to limit the scope of the invention as set forth in the appended claims. The invention is capable of other embodiments and of being practiced or of being carried out in various ways.

Further, no admission is made that any reference, including any patent or patent document, cited in this specification constitutes prior art. In particular, it will be understood that, unless otherwise stated, reference to any document herein does not constitute an admission that any of these documents form part of the common general knowledge in the prior art in the United States or in any other country. Any discussion of the references states what their authors assert, and the applicant reserves the right to challenge the accuracy and pertinence of any of the documents cited herein.

Throughout this disclosure, various aspects of this invention may be presented in a range format. It should be understood that the description in range format is merely for convenience and brevity, and should not be construed as an inflexible limitation on the scope of the invention. Accordingly, as will be understood by one skilled in the art, for any and all purposes, particularly in terms of providing a written description, all ranges disclosed herein also encompass any and all possible subranges and combinations of subranges thereof, as well as all integral and fractional numerical values within that range. As only one example, a range of 20% to 40% can be broken down into ranges of 20% to 32.5% and 32.5% to 40%, 20% to 27.5% and 27.5% to 40%, etc. Any listed range is also easily recognized as sufficiently describing and enabling the same range being broken down into at least equal halves, thirds, quarters, fifths, tenths, etc. As a non-limiting example, each range discussed herein can be readily broken down into a lower third, middle third, and upper third, etc. Further, as will also be understood by one skilled in the art, all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio. Further, the phrases "ranging/ranges between" a first indicate number and a second indicate number and "ranging/ranges from" a first indicate number "to" a second indicate number are used herein interchangeably. The foregoing are only examples of what is specifically intended.

Also, it is to be understood that the phraseology and terminology used herein is for the purpose of description and should not be regarded as limiting. The use of "comprising," "including," "having," and variations thereof herein is meant to encompass the items listed thereafter and equivalents thereof as well as additional items. "Comprising" encompasses the terms "consisting of" and "consisting essentially of." The use of "consisting essentially of" means that the composition or method may include additional ingredients and/or steps, but only if the additional ingredients and/or steps do not materially alter the basic and novel characteristics of the claimed composition or method. Unless specified or limited otherwise, the terms such as "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Unless otherwise noted, technical terms are used according to conventional usage. However, as used herein, the following definitions may be useful in aiding the skilled practitioner in understanding the invention:

As used herein, the terms "cellulosic feedstock", "cellulosic substrate" or "cellulosic material", are meant to refer to any type of biomass that contains cellulose. For example, cellulosic feedstocks may include grasses such as switch grass, cord grass, rye grass, miscanthus, or a combination thereof; sugar-processing residues such as sugar cane bagasse and sugar beet pulp; agricultural wastes such as soybean stover, corn stover; oat straw, rice straw, rice hulls, barley straw, corn cobs, wheat straw, canola straw, oat hulls, and corn fiber; and forestry wastes, such as recycled wood pulp fiber, sawdust, hardwood, softwood, or any combination thereof. Further, the cellulosic feedstock may include cellulosic waste or forestry waste materials such as newsprint, cardboard and the like. Cellulosic feedstock may also include one or more species of fiber that originate from different cellulosic feedstocks. Wheat straw, barley straw, corn stover, soybean stover, canola straw, switch grass, reed canary grass, sugar cane bagasse, cord grass, oat hulls, sugar beet pulp and miscanthus are particularly advantageous as cellulosic feedstocks due to their widespread availability and low cost.

The term "hydrolytic enzyme(s)" is meant to refer to enzymes that catalyze hydrolysis of biological materials such as cellulose. Hydrolytic enzymes include "cellulase enzymes" or "cellulases" (used interchangeably) which are enzymes that catalyze the hydrolysis of cellulose to products such as glucose, cellobiose, cello-oligodextrins, and other cello-oligosaccharides. "Cellulase" is meant to be a generic term denoting a multienzyme complex or family, including exo-cellobiohydrolases (CBH), endoglucanases (EG), and β-glucosidases (βG) that can be produced by a number of plants and microorganisms. It is noted that many crude cellulase extracts also include some hemicellulases. The process in accordance with embodiments of the invention may be carried out with any type of cellulase enzyme complex, regardless of their source; however, microbial cellulases are generally available at lower cost than those of plants. Among the most widely studied, characterized, and commercially produced cellulases are, e.g., those obtained from fungi of the genera *Aspergillus, Humicola*, and *Trichoderma*, and from the bacteria of the genera *Bacillus* and *Thermobifida*. Also, for example, cellulase produced by the filamentous fungi *Trichoderma longibrachiatum* includes at least two cellobiohydrolase enzymes termed CBHI and CBHII and at least 4 EG enzymes.

"Fermentation enzymes" refer to enzymes that can catalyze the conversion of the cellulosic sugars to alcohols, including ethanol as well as higher chain alcohols such as butanol. Typically, yeast such as *Saccharomyces cerevisiae* is used to produce the enzymes that catalyze the conversion. Enzymes may also include bacterial enzymes from *Clostridium acetobuytlicum* as well as enzymes produced by engineered microorganisms to produce the higher chain alcohols from the sugars of cellulose.

The term "degree of polymerization" (abbreviated as D.P.) refers to the number of D-glucose monomers in a cellulose molecule. Thus, the term "average degree of polymerization", or "average D.P.", refers to the average number of D-glucose molecules per cellulose polymer in a population of cellulose polymers.

As used herein, the terms "treatment," "treating," "pretreatment," or "pretreating" in respect of cellulose are meant to refer to a process or treatment in accordance with embodiments of the invention in which cellulose is made more accessible for enzymatic or chemical, e.g., chemical catalytic, reaction.

"Modification or degradation" in reference to cellulose is used to refer to the biological, e.g., enzymatic, or chemical-induced alteration of the native structure of cellulose. Such changes and alterations are known to those in the art and include those involved in enzymatic degradation and/or enzymatic or chemical hydrolysis of cellulose, as well as chemical modifications involved in a variety of commercial cellulose-based products, production of alcohols by fermentation of biomass, and generation of hydrogen-rich biofuels.

The term "stable" or "stabilizing" in regard to decrystallized cellulose refers to decrystallized cellulose that does not change materially over a selected period of time and under selected conditions.

Figure 1:
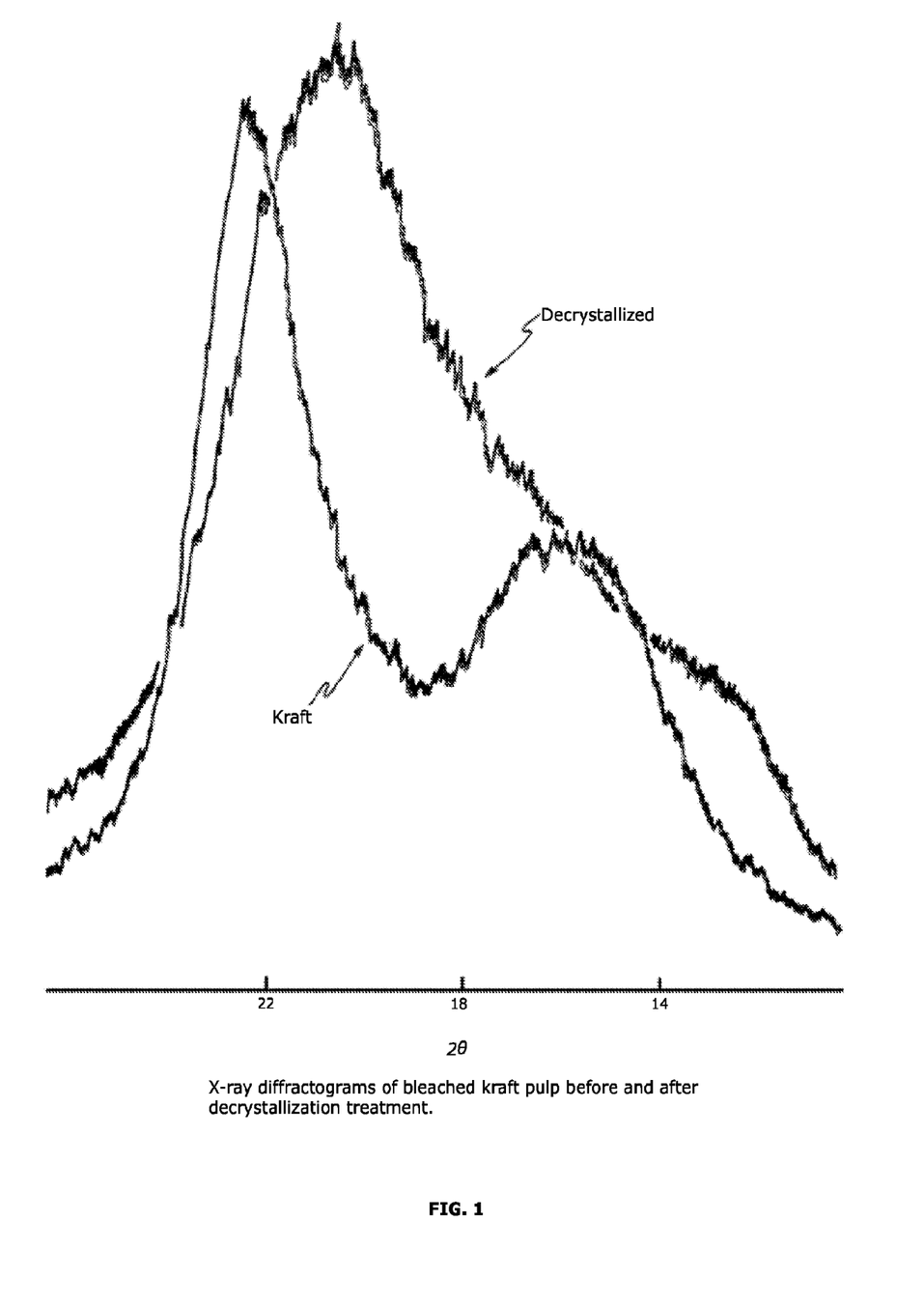
FIG. 1 is an x-ray diffractogram of a pulp before and after the pretreatment process in accordance with embodiments of the invention.

In view of the foregoing disadvantages inherent in conventional cellulose conversion, embodiments of the invention provide novel methods for decrystallizing or deaggregating cellulose. The methods include reacting cellulose with a treatment solution, which includes an alkali dissolved in a co-solvent system, under mild conditions of temperature and pressure that may be optimized for economic feasibility. Subjecting the cellulose to such treatment in accordance with embodiments of the invention makes the cellulose more accessible for enzymatic or chemical reaction, by opening up the tightly aggregated domains, which are also the source of recalcitrance during hydrolysis. The resulting decrystallized cellulose in accordance with embodiments of the invention also allows for much more uniform substitution along the cellulose chains, thus minimizing problems of quality control currently inherent in producing cellulose derivative products. Reference is made to FIG. 1, which shows an x-ray diffractogram of pulp before and after treatment in accordance with embodiments of the invention, demonstrating the decrystallization of the pulp.

There are many solvent systems that can swell native celluloses without solubilizing them. With the process in accordance with embodiments of the invention that opens up the semicrystalline cellulose domains, it is likely that a number of the systems that swell cellulose can be used to solubilize it, and thus, make possible cellulose regeneration in an economically competitive process.

As described above, the treatment solution in accordance with embodiments of the invention includes an alkali dissolved in a co-solvent system. Suitably, the alkali is dissolved in a co-solvent system of water plus a second water-miscible solvent. In one aspect, the second solvent is suitably an alcohol which may include, e.g., methanol, ethanol, propanol, isopropanol, butanol, isobutanol, or a polyol. In another aspect, the second solvent may include other protic solvents as well as aprotic solvents that are miscible in water. In an illustrated embodiment, the co-solvent system is ethanol and water.

In some embodiments of the invention, the alkali is suitably sodium hydroxide (NaOH), although other alkalis may be used, such as lithium hydroxide (LiOH) or potassium hydroxide (KOH). The concentration of NaOH needed in the treatment solution depends on the nature of the cellulose to be treated, as different celluloses may have their lattice forms disrupted at different concentrations of alkali. For example, the threshold for mercerization of most pulps is approximately 8% NaOH in water; for cotton, it is about 11 to 12%, depending on prior pretreatment; and for bacterial cellulose, it is about 14%.

Establishing the molarity of NaOH of the treatment solution is an iterative process. As a beginning point, the co-solvent ratio is fixed at a level that was found optimal in the finishing of cotton (4), which is reported to be 75% ethanol and 25% water. The molarity is then varied and the effectiveness of the treatment is assessed until an optimum molarity of the NaOH in the co-solvents is identified.

In Examples below, the effect of the solutions on Avicel, a microcrystalline cellulose prepared from northern softwood (American Viscose Company, Marcus Hook, Pa.) and pulped at 180° C., was compared with earlier observations on other celluloses. It was found that a molarity of NaOH solutions between 1 M and 2 M worked well. Avicel was selected for the testing because it has become the standard substrate used in most published studies of bioconversion of cellulose. Avicel is a highly recalcitrant cellulose and representative of the effects of elevated temperature on pulp crystallinity. In additional Examples, kraft pulps derived from a toilet paper were used. The toilet paper was of the type designed for use in septic systems so that it did not contain wet strength additives. The paper was made up of approximately 65% eucalyptus and 35% northern softwood. Use of an organosolv pulp (e.g., see, U.S. Pat. No. 4,100,016 to Diebold, et al.) is also included in the Examples below.

Once the approximately optimum molarity of NaOH is established, the optimal ratio of co-solvents is established. While 75% was chosen by earlier investigators, they did not explore the potential of 70% or of 80%. In varying the ratio, it is important to avoid levels of ethanol that can result in precipitation of NaOH.

Figure 2:
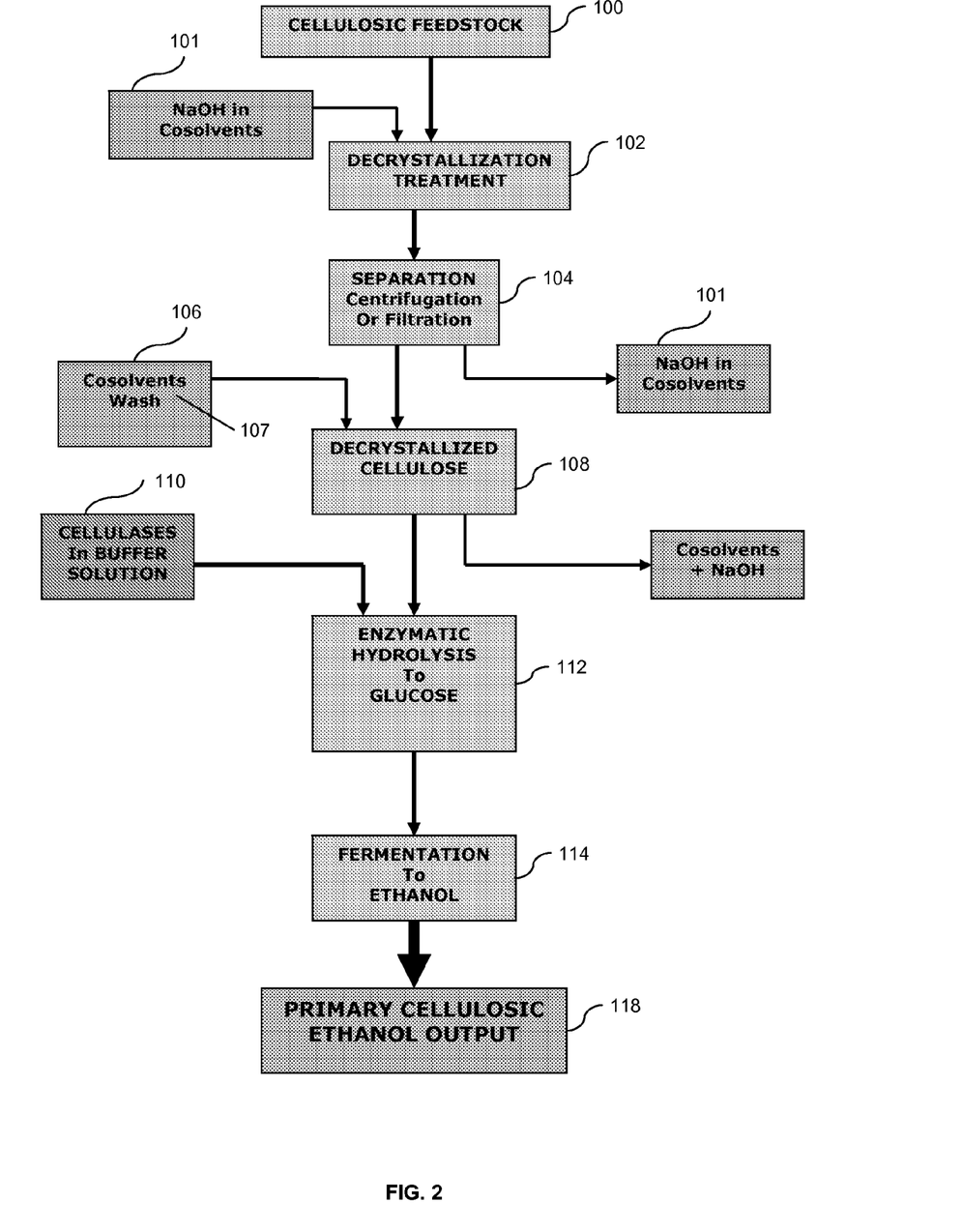
FIG. 2 is a flowchart illustrating a system in accordance with embodiments of the invention including the pretreatment of cellulosic feedstock to increase its accessibility to depolymerization.

Reference is now made to FIG. 2 that illustrates the general treatment process for embodiments in accordance with the invention as well as further steps in the processing of cellulosic feedstock to an alcohol, e.g., ethanol. The process begins at step 100 with a cellulosic source. In an illustrated embodiment, Avicel was used as a source of cellulose at step 100.

At step 102, the cellulosic material is subjected to a pretreatment step in accordance with embodiments of the invention, i.e., a treatment solution of alkali in a co-solvent system 101 of water and a second solvent, such as an alcohol, e.g., ethanol, or another water-miscible solvent, to decrystallize the cellulose. At step 104, the reaction mixture is separated to yield the decrystallized cellulose 108 and remove the treatment solution 101. At step 106, the treated cellulose is washed with a washing co-solvent solution or mixture 107 to remove the alkali. The washing co-solvent or mixture is suitably an alcohol/water mixture. At step 112, the treated cellulose in accordance with embodiments of the invention is hydrolyzed, for example, by treatment with cellulases 110, to form sugars. At step 114, the sugars, which include glucose and cello-oligodextrins, are suitably fermented, and a cellulosic alcohol 118 is recovered from the fermentation mix via distillation or other separatory method, e.g., membrane separation.

The effectiveness of the treatment solution is suitably measured by the onset of disruption of the Raman spectrum of cellulose, particularly in the low frequency region between 250 cm$^{-1}$ and 600 cm$^{-1}$ wherein the band at 378 cm$^{-1}$ is a very sensitive index of the degree of perturbation of the native lattice.

As to the washing mixture 107, if methanol was used as the co-solvent with water, it has been found that the same ratio of methanol to water as in the treatment co-solvent system is suitable for washing the NaOH out of the cellulose. For the ethanol/water system, a suitable ratio was also the same as in the treatment co-solvent.

It was noted earlier that the work with methanol was based on using the same ratio of co-solvents as in the pretreatment and was used as the starting point for ethanol/water co-solvent. The effect of varying the initial co-solvent for the first wash was determined. From a process perspective, it is especially suitable if the co-solvent ratio in the washing mixture is higher in ethanol than that used for the pretreatment as that would reduce the cost of post treatment of the washing solution. However, it is again noted that it is necessary to ensure that the ethanol content of the initial wash is not high enough to cause precipitation of NaOH.

After the first wash is completed, it is necessary to continue washing the cellulose substrate until a neutral pH is achieved. It was found in some cases that it was more effective to transition from the first wash to washes with co-solvents including higher levels of water, before eventually washing with water only.

Figure 3:
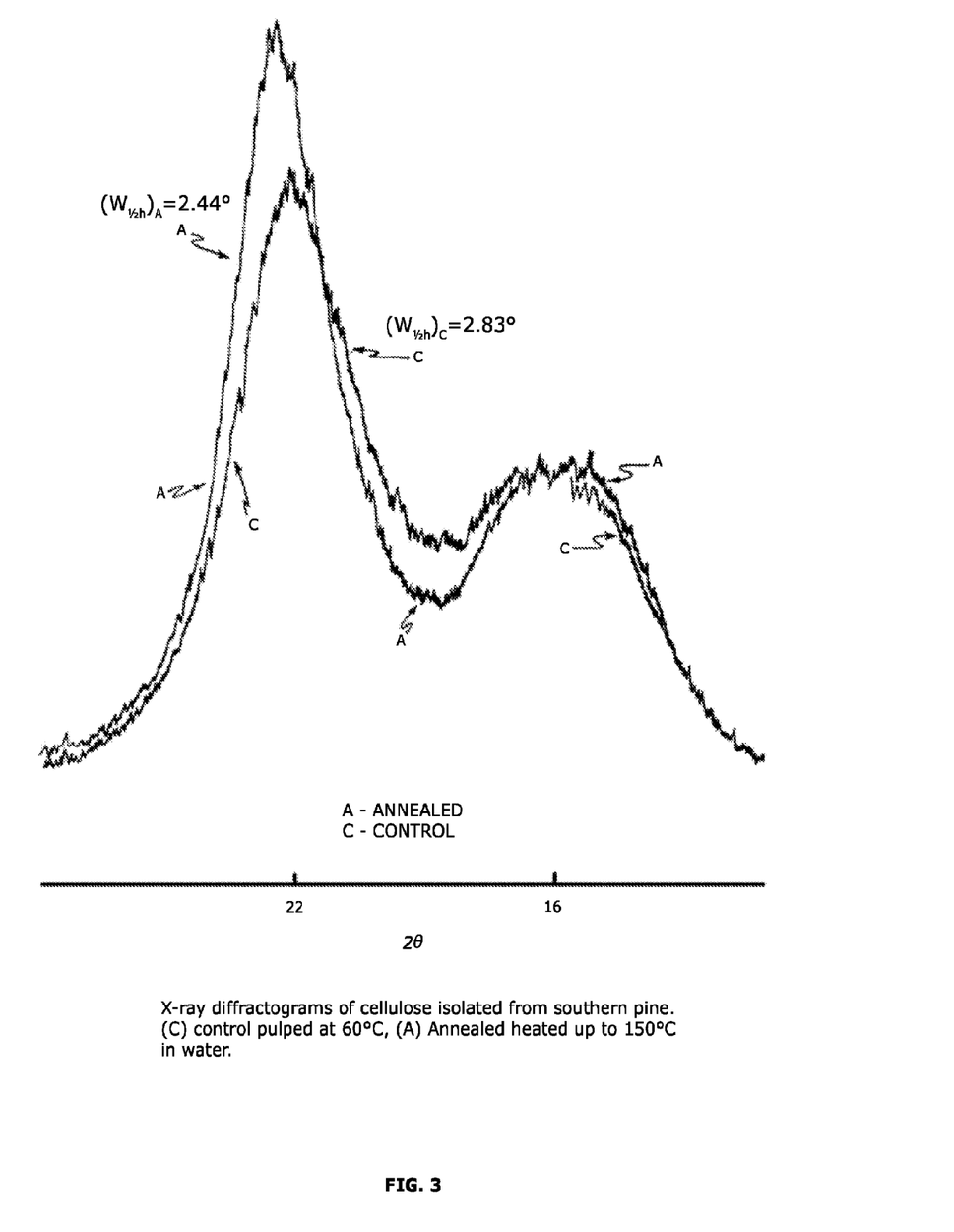
FIG. 3 shows comparative x-ray diffractograms of a cellulose isolated at 70° C. before and after it is annealed at 150° C.
Figure 4:
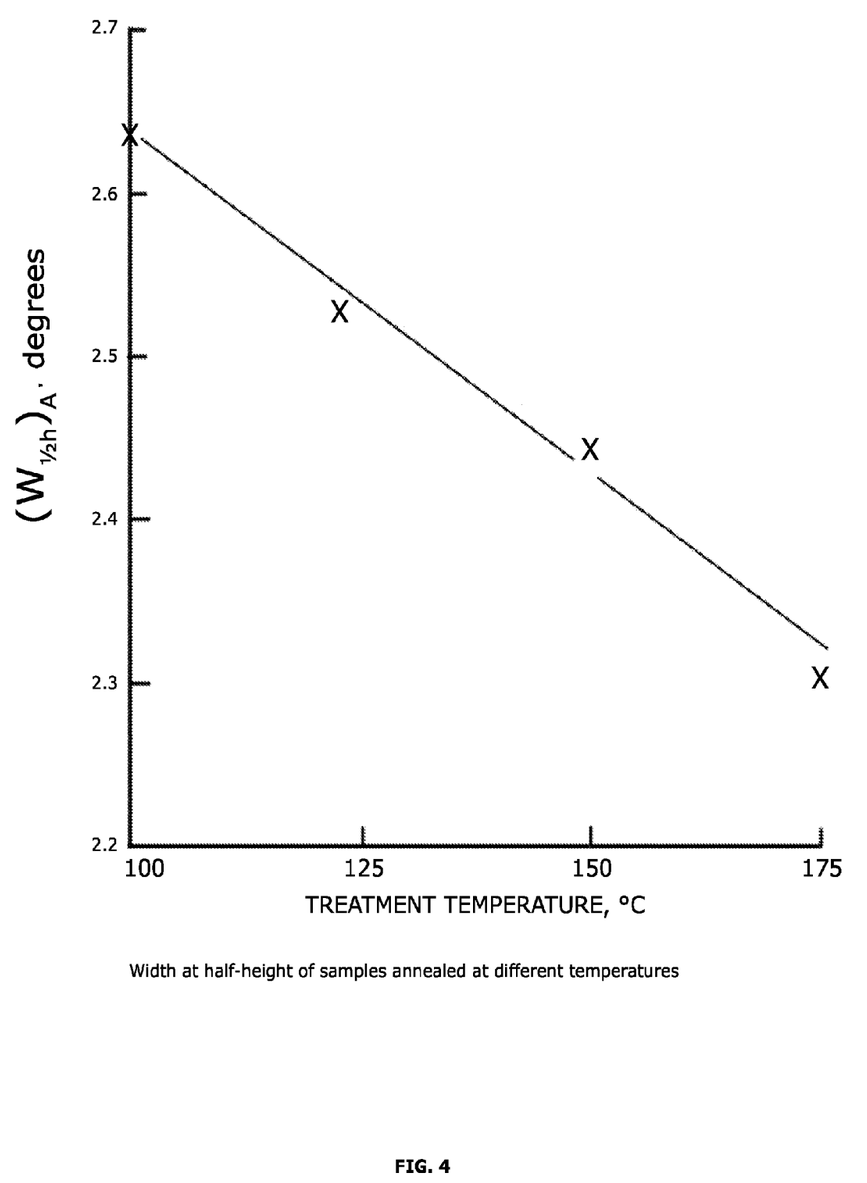
FIG. 4 is a graph of the width at half-height of cellulose samples annealed at different temperatures.

It has also been found that the degree to which the cellulose is tightly aggregated, and hence, its recalcitrance, is related to the highest temperature to which the cellulose is exposed during isolation (5). See, FIGS. 3 and 4 taken from the Atalla et al. reference (5). FIG. 3 shows the dramatic reduction in the width at half-height of the primary diffraction peak of native celluloses as a result of the annealing at 150° C. The width at half-height for the most prominent reflection in powder diffraction patterns of wood celluloses has always been regarded as one of the most sensitive indices of the degree of coherence of order within the cellulose in the wood cell walls. FIG. 4 shows how the width at half height declines as the temperature of treatment increases. Thus, in essence, the recalcitrance of a cellulosic sample is directly correlated with the temperature of isolation.

Once treated and washed, the degree to which the treated cellulose has become more accessible, i.e., decrystallized, can be assessed. Simple analytical methods, such as the weight loss upon enzymatic hydrolysis, can and were used as the measure of success in decrystallizing cellulose. Methods utilizing accessibility to deuterium oxide ($D_2O$) of the decrystallized cellulose can also be used. While these methods can rank the treatments, the readiness with which deuterium exchanges with hydrogen suggests that the use of $D_2O$ may result in overstating the degree of accessibility. It has been found that deuterated ethylene glycol ($OHCD_2CD_2OH$) appropriately assesses the degree of accessibility to enzymatic action.

In utilizing deuterated methods, the most common measures of accessibility have relied on observation of the access to cellulosic hydroxyl groups on the basis of perfusion of samples with $D_2O$ (4). While this is a useful measure, a more reliable measure is based on accessibility to molecules larger than the $D^+$ ion. Such molecules suitably include perdeutero methanol ($CD_3OH$), perdeutero ethylene glycol ($CD_2OHCD_2OH$), and perdeutero glycerol ($CD_2OHCDOHCD_2OH$), which can be added to the pretreated cellulosic samples in solution in $H_2O$, and allowed to reach equilibrium. The amount of deuterated molecules within the cellulosic samples is monitored through measurement of the Raman spectra of the samples in the region between 2300 and 2700 cm$^{-1}$ where there will be no interference from any other functional groups. The preparation of the perdeuterated samples of the alcohols or polyols can be accomplished by refluxing in $D_2O$ over Raney nickel.

Perdeuterated methanol is available commercially, and perdeuteration of glycol and glycerol can be carried out as noted above. The perdeuterated methanol is used in measurements based on using other celluloses that are common standards such as Avicel, which is derived from dissolving pulps, and Whatman CF-1 powder, which is derived from cotton linters. These standards are pre-swollen using known protocols.

As most enzymes are much larger in size than the molecules used to assess cellulose accessibility, an assay was developed for the transformations of the celluloses more closely related to the activity of enzymes. In such assay, the pretreated and washed cellulose are incubated with representative cellulases from *Aspergilus niger* and *Trichoderma reesi* to assess the effect of the transformations on susceptibility to enzyme action. As noted earlier, the increased availability of celluloses to the hydrolytic enzymes should increase the rate of conversion to sugars by at least one order of magnitude or more.

Reference is again made to FIG. 2 wherein it is noted that a portion of the alcohol, e.g., ethanol, produced, i.e., reference numeral 118, can be used in the decrystallization step 102 as the co-solvent. Thus, in accordance with embodiments of the invention, the entire cellulose conversion process may suitably have a feedback loop to supply co-solvent for the pretreatment process.

It is noted that a barrier to economic implementation of enzymatic hydrolysis of celluloses is the biphasic nature of the process when the celluloses are subjected to hydrolytic enzymes on a continuous basis in a batch process. The very long residence times required for the second phase result in the need for very large holding tanks to accommodate the time needed for the second phase to be complete. In another embodiment, it is envisioned that the long residence times of enzymatic hydrolysis reactions due to its biphasic nature can be reduced by use of the treatment process in accordance with embodiments of the invention. To overcome this barrier, the application of the enzymes can suitably be accomplished in multiple stages, with the cellulosic substrates subjected to the treatment in accordance with embodiments of the invention between stages.

Figure 5:
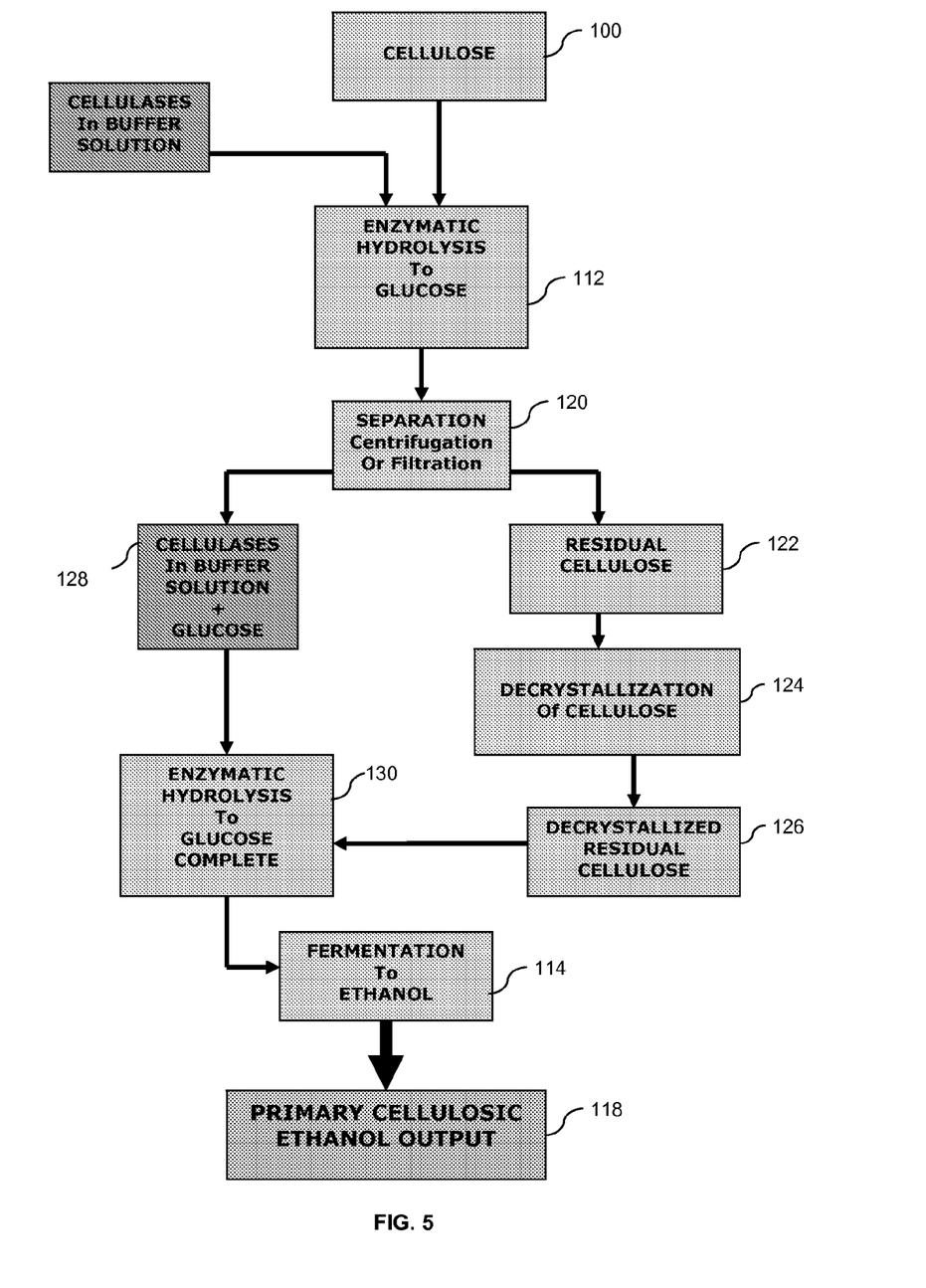
FIG. 5 is a flow chart describing an embodiment wherein the enzymes are applied without prior pretreatment followed by separation of the residual cellulose, pretreatment according principles of the invention, and then recombination with the supernatant from the separation after the first stage.

At least three such multistage processes are contemplated. As shown in FIG. 5, a first application of enzymatic hydrolysis is carried out in a first stage prior to a pretreatment as described herein in order to take advantage of the relatively rapid early phase in enzymatic hydrolysis. When the rate of hydrolysis has slowed down at the beginning of the second phase, the solid cellulosic residue is separated and pretreated as described herein, and then recombined with the supernatant liquid stream separated from the solids at the end of the first phase. Specifically, a cellulosic material 100 is subjected to enzymatic hydrolysis 112 with cellulose until the first phase of enzymatic hydrolysis begins to slow. At step 120, the reaction mixture is separated into residual cellulose 122 and the remainder 128 of cellulases and glucose. The residual cellulose 122 is subjected to the decrystallization 124 as illustrated in FIG. 2, to yield a decrystallized residual cellulose 126 which is subjected to enzymatic hydrolysis 130 again, utilizing remainder enzymatic solution 128. The sugar products are then fermented at step 114 to produce cellulosic ethanol 118.

Figure 6:
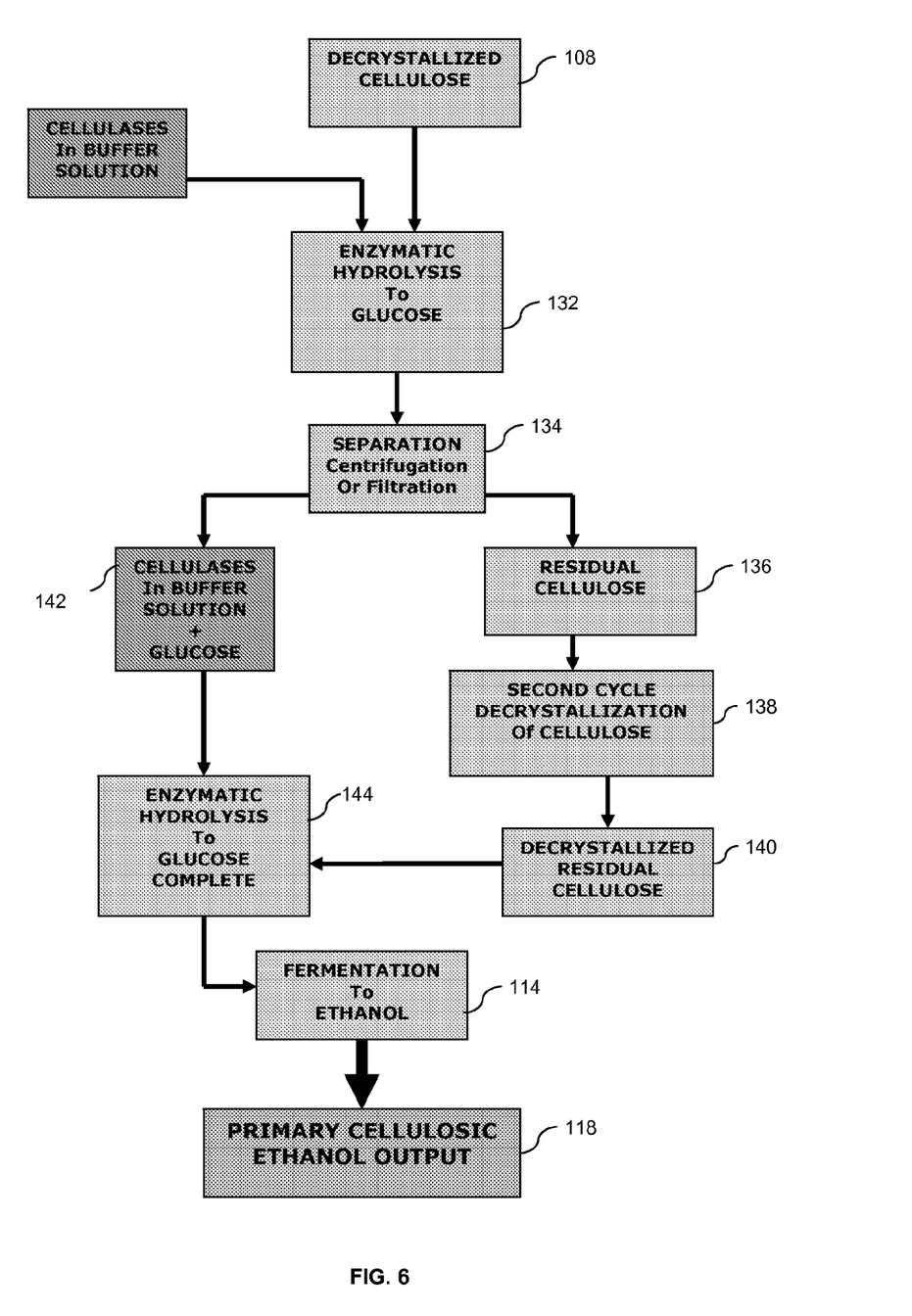
FIG. 6 is a flowchart illustrating an alternative embodiment for reducing enzymatic reaction times in accordance with principles of the invention, including treating the residual cellulose from a first stage pretreatment with second stages of decrystallization and enzymatic hydrolysis to glucose before fermentation to ethanol.

An embodiment of a second multistage process is shown in FIG. 6, and is based on repeating the decrystallization process as described herein between hydrolytic stages. At step 132, a decrystallized cellulose 108 as described herein is exposed to the enzymes for a period corresponding to the early phase of rapid hydrolysis. Next, at step 134, the residual cellulose 136 is separated from the enzyme-containing liquid medium 142 by filtration or centrifugation. The residual cellulose 136 is then subjected to a second cycle of decrystallization at step 138, as illustrated in FIG. 6, to yield a decrystallized residual cellulose 140, which, in turn, is exposed again to the enzyme-containing buffered water solution 142 for enzymatic hydrolysis to glucose at step 144 before fermentation to cellulosic ethanol 118 at step 114. It is anticipated that the hydrolysis again proceeds at a rapid rate so that the hydrolysis of the cellulose can be completed in a much shorter period than in the case of a single stage hydrolysis. Thus, one of the major cost factors in processes based on current designs, which need very long holding periods or residence times in the enzyme solution, is overcome and significantly reduced.

Figure 7:
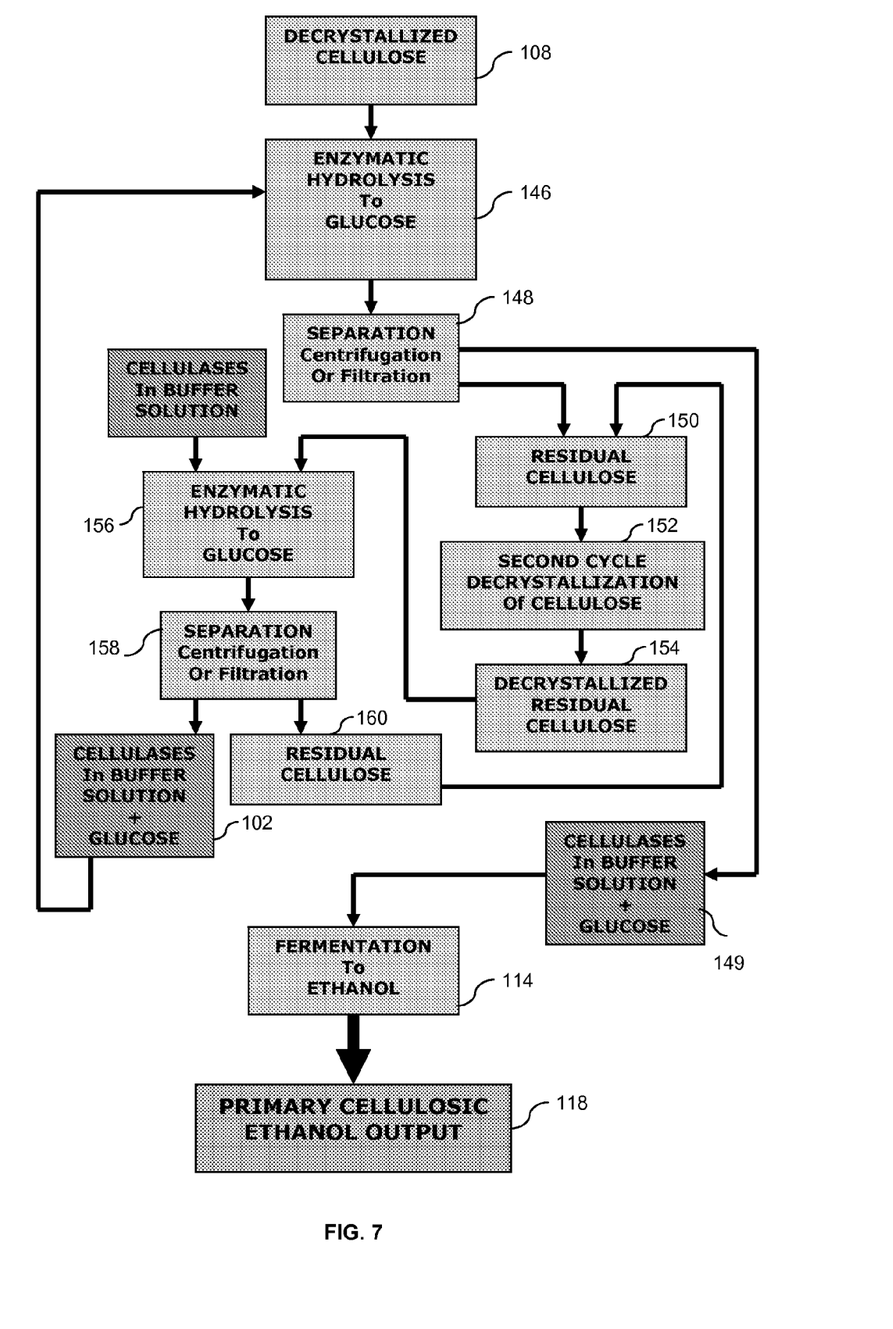
FIG. 7 is a flowchart illustrating yet another embodiment for reducing enzymatic reaction times in accordance with principles of the invention utilizing a countercurrent system wherein the residual cellulose from the second stages of treatment is recirculated into the first stage of pretreatment.

An embodiment of a third multistage process is shown in FIG. 7, and includes a countercurrent mixing of the cellulose and the enzyme solutions. At step 146, a decrystallized cellulose 108 as described herein, is exposed to the enzymes. At step 148, the residual cellulose 150 is separated from the enzyme-containing liquid medium 149 by filtration or centrifugation. The residual cellulose 150 is subjected to a second cycle of decrystallization at step 152 to yield a decrystallized residual cellulose 154, which in turn is exposed again to the enzyme-containing buffered water solution at step 156. As shown in FIG. 7, fresh enzyme may be used at step 156 in the second stage of treatment, and after the second stage of treatment, the residual cellulose 160 is separated at step 158, and then introduced into a second cycle of decrystallization 152 to yield a decrystallized residual cellulose 154, and then reintroduced into the enzymatic solution 156. Furthermore, after filtration or complete dissolution at step 158 of the cellulose, the enzyme solution 102 is re-applied to decrystallized cellulose at step 146. The sugar products are then fermented at step 114 to produce cellulosic ethanol 118. Such an approach reduces the amount of enzyme needed for the conversion of the cellulose to glucose. The cost of the enzymes is another major economic barrier for processes based on current designs.

The specific embodiment in this third multistage process will depend on the nature of the cellulosic feedstock. If the cellulose was relatively pure, it is anticipated that the conversion may be complete before the enzyme-containing solution is added to the freshly decrystallized cellulose. However, if the feedstock contains other components of lignocellulosic matter, a filtration or centrifugation stage would be required prior to using the enzyme solution from the second stage to treat the feedstock in the first stage.

An embodiment of the invention is also contemplated as a kit, the kit including an alkali in an alcohol/water co-solvent, cellulase enzymes, one or more flocculants, and instructions for decrystallizing the cellulose to produce a decrystallized cellulose and instructions for hydrolyzing the decrystallized cellulose to produce a hydrolysis product.

It is further envisioned that a similar treatment may make the cellulose more accessible to solutions of homogeneous catalysts that may be used to transform the cellulosic feedstock into other forms. For example, the decrystallized cellulose as described herein could be more easily penetrated by the catalytic systems to reform it into hydrocarbons. Such process could make possible use of the vast amount of cellulosic resources as feedstocks for catalytic reformation to generate biofuels, such as diesel, fuel gases, such as hydrogen, and other high-value chemical types. Thus, in some embodiments, a method of producing cellulosic biofuels is provided. The method includes treating a cellulosic material with an alkali in an alcohol/water co-solvent system to yield a decrystallized cellulose; washing the decrystallized cellulose to remove the alkali; hydrolyzing the cellulose to glucose and cello-oligodextrins; and catalytically reforming the glucose and cello-oligodextrins into hydrocarbons.

As noted above, a barrier to much broader use of cellulose as a feedstock in the manufacture of fibers or films is the difficulty in solubilizing the cellulose in an environmentally acceptable system. The systems most often used outside of the United States are based on the century-old cellulose xanthate process, which is environmentally objectionable because the regeneration of the cellulose from solution results in the formation of hydrogen sulfide, and other toxic byproducts. The more recently developed methyl morpholine-N-oxide system relies on a complex and expensive solvent that is prone to explosion if conditions are not carefully controlled. On the other hand, the co-solvent system used herein is environmentally benign. It is envisioned that this system could alter dramatically the economics of rayon and cellophane manufacture as well as biofuels as described herein.

The following Examples, which should not be construed by way of limiting the scope of the invention, further explain embodiments of the invention. Moreover, all experimental processes may be further optimized for efficiency and the process of scale up is expected to achieve greater enhancement of efficiency of conversion of cellulose to sugars.

EXAMPLES

Experiments to demonstrate reduction of the recalcitrance of cellulose were carried out in two stages. The first included the process of treatment of the native cellulose. The second assessed the consequence of this treatment by exposing the treated cellulose samples to hydrolytic enzymes and measuring its weight loss in comparison to a control consisting of the untreated native cellulose from the same source.

The cellulose chosen as the substrate for the first Example was from a sample of Avicel PH1, which has been used as a standard in the inventor's laboratory since the 1970s and was supplied by the American Viscose Company (Marcus Hook, Pa.). It is a microcrystalline cellulose usually manufactured by acid hydrolysis of a high purity dissolving grade northern softwood pulp followed by mechanical disintegration of the pulp fibers and spray drying of the resulting dispersion of fiber fragments. This type of cellulose was chosen because Avicel has become a standard substrate in studies of enzymatic hydrolysis of cellulose and is representative of the most recalcitrant pulp-derived celluloses. In a second set of Examples, a kraft pulp derived from toilet paper was used. In yet another Example, an organosolv pulp was used.

The enzymes used in the assessments were a cellulase from the fungus *Trichoderma reesi* purchased from Worthington and a glucosidase derived from almonds available from Sigma Aldrich.

Example 1

Decrystallization

A solution prepared for treatment of the Avicel was a 1.5 N solution of sodium hydroxide (NaOH) in a mixture of ethanol ($CH_3CH_2OH$) and water that was 75% ethanol by volume. To prepare the treatment solution, ethanol and water were mixed, and then 6 g of NaOH was dissolved per 100 mL of the solvent mixture.

The treatment procedure was as follows: 1 g of Avicel was placed in a 300 mL beaker. To this, 50 mL of the treatment solution were added. The Avicel was allowed to sit in the treatment solution for 15 minutes. Thereafter, the solution was decanted and replaced with 100 mL of the solvent mixture (75% ethanol, 25% water). This solution was allowed to sit for a few minutes to allow diffusion of the NaOH out of the cellulose.

The solvent was then decanted and the process repeated two times whereupon the pH was approximately 8. After decanting the solvent the last time, a solution of 0.05 M ammonium acetate buffer at a pH of 5 was added; the pH was 5.4 after the rinse in buffer. The buffer solution was decanted, and 30 mL of buffer added again; the pH was then determined to be 5.0.

The dispersion of cellulose in 30 mL of buffer was transferred to a 50 mL polypropylene centrifuge tube and buffer added to the 40 mL level. Hydrolytic enzymes were added to the tube. These enzymes were 0.2 g cellulase (108 μ/mg) and 0.1 g β-glucosidase (6 μ/mg).

A control sample of 1 g of untreated Avicel was also placed in a 50 mL polypropylene centrifuge tube, and 40 mL of buffer added to it, followed by addition of the same amounts of enzymes as the test sample.

The two centrifuge tubes were then tightly closed with their covers, and inserted in a Vortemp 1550 shaking incubator. The contents of the tubes were incubated at 45° C. and agitated at a speed of 900 rpm. It was found necessary to agitate at 900 rpm to keep the cellulose microcrystalline particles adequately dispersed.

For a first experiment, the incubation was for 41 hrs, and for a second, the incubation was for 13 hrs.

After the incubation, the two dispersions were each divided into 8 portions in 15 mL centrifuge tubes. The tubes were inserted in a centrifuge and spun for 2 minutes at 3800 rpm. The buffer-enzyme liquid was decanted from each tube and replaced with 95% ethanol, re-dispersed and spun again; this was done twice for each of the samples. The last ethanol decanted was replaced with acetone followed by dispersion in the acetone.

The acetone dispersions were then, in turn, poured into tared crucibles with sintered glass bottom filters; the crucible filters were mounted on a vacuum flask with full vacuum applied during the filtration. The crucibles were then transferred to a vacuum oven with full vacuum applied, heated to 105° C., and held at that temperature under vacuum overnight.

The samples were then weighed on an analytical balance, and the weight loss taken as a measure of the conversion of cellulose to glucose and soluble oligomers.

It should be noted that the 1.5 M (or 1.5 N) solution of NaOH in the solvent mixture was selected because the Avicel microcrystalline cellulose was derived from a dissolving pulp. Had microcrystalline cellulose made from cotton linters been used, it would have been necessary to use a 2 M (or 2 N) solution of NaOH in the solvent. Conversely, if the cellulose had been isolated from a herbaceous plant at a temperature much closer to ambient temperature, a 1 M (or 1 N) solution may have been adequate. This variability in the normality required for the pretreatment of cellulose reflects the great diversity in the level of aggregation of celluloses from different sources and with different histories into semicrystalline domains.

Results:

As noted above, the initial weights of the test and control samples were 1 g each. The weights after exposure to the enzyme mixture at 45° C. are given below in Table 1.

TABLE 1

| Incubation time | Control | Pretreated | Δ |
|---|---|---|---|
| 13 hrs | 0.535 g | 0.408 g | 0.127 g |
| 41 hrs | 0.251 g | 0.189 g | 0.062 g | where Δ represents the difference in weight loss between the control and pretreated samples. Thus, in both instances the loss in weight of the sample treated as described herein was significantly greater than that of the control sample.

The results demonstrated that the loss in weight for both samples during the first 13 hr exposure was significantly higher than the loss during the further exposure for an additional 28 hrs. This is typical of the biphasic nature of enzyme action on celluloses where the rate of conversion to glucose or soluble oligomers proceeds rapidly at first but then levels off to a much slower rate. The results of these experiments demonstrate that the decrystallization treatment described herein increases the disorder in cellulose substrates, and makes them more susceptible to enzymatic hydrolysis by cellulases.

Example 2

A Two Stage Process

A solution prepared for treatment of the Avicel was a 1.5 N solution of sodium hydroxide (NaOH) in a mixture of ethanol ($CH_3CH_2OH$) and water that was 75% ethanol by volume. To prepare the treatment solution, one mixes the ethanol and water, and then dissolves 6 g of NaOH per 100 mL of the solvent mixture.

The treatment procedure was as follows: 2 samples of 1 g each of Avicel were placed in 50 mL centrifuge tubes, one experimental sample, and one control. To each, 45 mL of 0.05 N ammonium acetate buffer with a pH of 5.01 was added. Both tubes received 0.15 g of cellulase, which was assayed at 136 μ/mg DW, with no supplemental β-glucosidase.

Both samples were placed in a Vortemp 1550 shaking incubator. They were incubated at 50° C. and agitated at a speed of 900 rpm. Initial incubation was for 5.5 hours.

After the initial incubation period, the experimental sample was removed from the incubator and chilled in an ice bath to halt the enzyme action. The experimental sample was then placed in a centrifuge and spun at 4500 rpm to extract the supernatant. The supernatant was decanted and set aside for later return to the sample tube.

The sample tube then had 50 mL of the NaOH treatment solution added, and was shaken for 5 minutes, after which it was placed back in the centrifuge to extract the treatment solution.

Thereafter, the solution was decanted and replaced with 50 mL of the solvent mixture (75% ethanol, 25% water). It was shaken for 5 minutes to allow diffusion of the NaOH out of the cellulose. It was then centrifuged at 4500 rpm.

The solvent was then decanted and the process repeated two times. After the last decanting of solvent, a solution of 0.05 M ammonium acetate buffer at a pH of 5.01 was added; the pH was 8.4 after dispersing the sample in buffer. The buffer solution was centrifuged and decanted and 40 mL of buffer added again; the pH was then determined to be 5.15. This cycle was repeated one more time, after which the pH of the sample in buffer was 5.04. The buffer was then removed.

The supernatant enzyme solution extracted previously was returned to the sample tube, and incubation was resumed at 50° C. and 900 rpm. The second phase of incubation lasted 2.5 hours.

After the incubation, both experimental and control sample tubes were inserted in a centrifuge and spun for 2 minutes at 4500 rpm. The buffer-enzyme liquid was decanted from each tube, and the remaining solids poured onto tared fiberglass paper for drying in a microwave oven with a built-in analytical balance, with the weight loss taken as a measure of the conversion of cellulose to glucose and soluble oligomers.

Results:

As noted above, the initial weights of the test and control sample were 1 g each. The weight after exposure to the enzyme mixture at 50° C. is given below in Table 2.

TABLE 2

| Incubation time | Control | Pretreated | Δ |
|---|---|---|---|
| 8 hrs | 0.529 g | 0.269 g | 0.26 g | where Δ represents the difference in weight loss between the control and pretreated samples. Thus, the loss in weight of the sample treated as described herein was significantly greater than that of the control sample.

Example 3

A Two Stacie Treatment Using a Kraft Pulp Paper

A solution prepared for treatment of toilet paper (Cottonelle™ brand) was a 1.5 N solution of sodium hydroxide (NaOH) in a mixture of ethanol ($CH_3CH_2OH$) and water that was 75% ethanol by volume. Preparation of the treatment solution was the same as described in previous examples The treatment procedure was as follows: 2 samples (one control and one experimental sample) of toilet paper were weighed and then cut into small pieces and placed in 50 mL centrifuge tubes. The tubes were filled with water and put in a Vortemp 1550 shaking incubator at room temperature at 900 rpm and left to disperse overnight.

Each tube was filled to the 50 mL mark with 0.05 N ammonium acetate buffer with a pH of 5.01. Both tubes received 0.125 g of cellulase, which was assayed at 136 μ/mg DW, with no supplemental β-glucosidase. Both samples were placed in the Vortemp incubator. They were incubated at 50° C. and agitated at a speed of 900 rpm. Initial incubation was for 4.25 hours.

After the initial incubation period, both samples were removed from the incubator and chilled in an ice bath to halt the enzyme action. The experimental sample was then placed in a centrifuge and spun at 4500 rpm to extract the supernatant. The supernatant was decanted and set aside for later return to the sample tube.

The sample tube then had 50 mL of the NaOH treatment solution added, and was shaken for 2 minutes, after which it was placed back in the centrifuge to extract the treatment solution.

Thereafter, the solution was decanted and replaced with 50 mL of the solvent mixture (75% ethanol, 25% water). It was shaken for 2 minutes to allow diffusion of the NaOH out of the cellulose.

The solvent was then decanted and the process repeated two times. After decanting the solvent the last time, a solution of 0.05 M ammonium acetate buffer at a pH of 5.01 was added; the pH was 6.4 after dispersing the sample in buffer. The buffer solution was centrifuged and decanted and 40 mL of buffer added again; the pH was then determined to be 5.23. The supernatant enzyme solution extracted previously was returned to the sample tube, and incubation was resumed at 50° C. and 900 rpm. The second phase of incubation lasted approximately 9.5 hours.

After the incubation, both experimental and control sample tubes were inserted in a centrifuge and spun for 2 minutes at 4500 rpm. The buffer-enzyme liquid was decanted from each tube, and the remaining solids poured onto tared fiberglass paper for drying in a microwave oven with a built-in analytical balance, with the weight loss taken as a measure of the conversion of cellulose to glucose and soluble oligomers.

Results:

The initial weights of the test and control samples, along with the weights after exposure to the enzyme mixture at 50° C. are given below in Table 3.

TABLE 3

|  | Initial wt | Final wt | % conversion |
|---|---|---|---|
| Control | 1.021 g | 0.314 g | 69.25% |
| Pretreated | 1.026 g | 0.226 g | 77.97% |

The difference in the percentage of sample weight remaining demonstrates that conversion of the sample treated as described herein was greater than that of the control sample.

Example 4

A Single Stage Treatment Using a Kraft Pulp Paper

A solution prepared for treatment of toilet paper (Cottonelle™ brand) was a 1.5 N solution of sodium hydroxide (NaOH) in a mixture of ethanol ($CH_3CH_2OH$) and water that was 75% ethanol by volume. Preparation of the treatment solution was the same as described in previous examples.

The treatment procedure was as follows: 2 samples (one control and one experimental sample) of toilet paper were weighed and then cut into small pieces and placed in 50 mL centrifuge tubes. The tubes were filled with water and put in a Vortemp 1550 shaking incubator at room temperature at 900 rpm and left to disperse overnight.

The experimental sample was put in a centrifuge for 2 minutes at 4500 rpm and the extracted water decanted. The tube was refilled with 200 proof ethanol, and shaken for 5 minutes at 900 rpm, after which the tube was centrifuged again, the ethanol decanted, and then the tube was refilled with a mix of 75% ethanol and 25% water, shaken for 5 minutes, centrifuged and decanted again.

The sample tube then had 50 mL of the NaOH treatment solution added, and was shaken for 5 minutes, after which it was placed back in the centrifuge to extract the treatment solution.

Thereafter, the solution was decanted and replaced with 50 mL of the solvent mixture (75% ethanol, 25% water). It was shaken for 5 minutes to allow diffusion of the NaOH out of the cellulose.

The solvent was then decanted and the process repeated two times. After decanting the solvent the last time, a solution of 0.05 M ammonium acetate buffer at a pH of 5.01 was added; the pH was 12.63 after dispersing the sample in buffer. The buffer solution was centrifuged and decanted and 40 mL of buffer added again; the pH was then determined to be 9.37. This cycle was repeated 4 more times, with the pH determined at 6.02, 5.29, 5.14, and then 5.05 in the last cycle.

The control tube was filled to the 50 mL mark with the same ammonium acetate buffer solution. Both tubes received 0.125 g of cellulase, which was assayed at 136 μ/mg DW, with no supplemental β-glucosidase. Both samples were placed in a Vortemp 1550 shaking incubator. They were incubated at 50° C. and agitated at a speed of 900 rpm for a total incubation of 16 hours and 25 minutes.

After the incubation, both experimental and control sample tubes were inserted in a centrifuge and spun for 2 minutes at 4500 rpm. The buffer-enzyme liquid was decanted from each tube, and the remaining solids poured onto tared fiberglass paper for drying in a microwave oven with a built-in analytical balance, with the weight loss taken as a measure of the conversion of cellulose to glucose and soluble oligomers.

Results:

The initial weights of the test and control samples, along with the weights after exposure to the enzyme mixture for 16 hours and 25 minutes at 50° C. are given below in Table 4.

TABLE 4

|  | Initial wt | Final wt | % conversion |
|---|---|---|---|
| Control | 1.020 g | 0.367 g | 64.02% |
| Pretreated | 1.017 g | 0.225 g | 77.88% |

The difference in the percentage of sample weight remaining demonstrates that conversion of the sample treated as described herein was greater that of the control sample.

Example 5

A Two Stacie Treatment Using an Organosolv Pulp

An organosolv pulp (e.g., U.S. Pat. No. 4,100,016) was initially treated with sodium chlorite to delignify it, after which it was allowed to air dry. The sodium chlorite treatment is a well-established, mild bleaching technique. Two samples (one control and one experimental sample) were weighed out from the resulting delignified, dried pulp.

A solution prepared for treatment of the delignified organosolv pulp was a 1.5 N solution of sodium hydroxide (NaOH) in a mixture of ethanol ($CH_3CH_2OH$) and water that was 75% ethanol by volume. Preparation of the treatment solution was the same as described in previous examples.

The treatment procedure was as follows: 2 samples (one control and one experimental sample) of pulp were weighed and then placed in 50 mL centrifuge tubes. The tubes were filled with water and put in a Vortemp 1550 shaking incubator at room temperature at 900 rpm and left to disperse for two days. After dispersion, both tubes were put in a centrifuge and spun at 4500 rpm for about 3 minutes, after which the water was decanted.

Each tube was then filled to the 50 mL mark with 0.05 N ammonium acetate buffer with a pH of 5.01. Both tubes received 0.2 g of cellulase, which was assayed at 136 μ/mg DW, with no supplemental β-glucosidase. Both samples were placed in the Vortemp incubator. They were incubated at 50° C. and agitated at a speed of 900 rpm. Initial incubation was for 5.5 hours.

After the initial incubation period, both samples were removed from the incubator. The experimental sample was then placed in a centrifuge and spun for 7 minutes at 4700 rpm to extract the supernatant. The supernatant was decanted and set aside for later return to the sample tube.

The sample tube then had 50 mL of the NaOH treatment solution added, and was shaken for 2 minutes, after which it was placed back in the centrifuge to extract the treatment solution.

Thereafter, the solution was decanted and replaced with 50 mL of the solvent mixture (75% ethanol, 25% water). It was shaken for 2 minutes to allow diffusion of the NaOH out of the cellulose.

The solvent was then decanted and the process repeated two times. After decanting the solvent the last time, a solution of 0.05 M ammonium acetate buffer at a pH of 5.01 was added; the pH was 7.32 after dispersing the sample in buffer. The buffer solution was centrifuged and decanted and 40 mL of buffer added again; the pH was then determined to be 5.18.

The supernatant enzyme solution extracted previously was returned to the sample tube, and incubation was resumed at 50° C. and 900 rpm. The second phase of incubation lasted approximately 3.5 hours.

After the incubation, both experimental and control sample tubes were inserted in a centrifuge and spun for 2 minutes at 4500 rpm. The buffer-enzyme liquid was decanted from each tube, and the remaining solids poured onto tared fiberglass paper for drying in a microwave oven with a built-in analytical balance, with the weight loss taken as a measure of the conversion of cellulose to glucose and soluble oligomers.

Results:

The initial weights of the test and control samples, along with the weights after exposure to the enzyme mixture at 50° C. are given below in Table 5.

TABLE

|  | Initial wt | Final wt | % conversion |
|---|---|---|---|
| Control | 1.003 g | 0.539 g | 46.26% |
| Pretreated | 1.005 g | 0.409 g | 59.3% |

The difference in the percentage of sample weight remaining demonstrates that conversion of the sample treated as described herein was greater than that of the control sample.

The foregoing description is considered as illustrative only of the principles of the invention. Further, since numerous modifications and changes may readily occur to those skilled in the art, it is not desired to limit the invention to the exact construction and operation shown and described, and accordingly, all suitable modifications and equivalents are considered to fall within the scope of the invention. Various features and advantages of the invention are set forth in the following claims.

All publications, patents and patent applications referenced in this specification are indicative of the level of ordinary skill in the art to which this invention pertains. All publications, patents and patent applications are herein expressly incorporated by reference to the same extent as if each individual publication or patent application was specifically and individually indicated by reference. In case of conflict between the present disclosure and the incorporated patents, publications and references, the present disclosure should control.

REFERENCES

1. "Breaking the Biological Barriers to Cellulosic Ethanol: A Joint Research Agenda" A Research Roadmap Resulting from the Biomass to Biofuels Workshop, Dec. 7-9, 2005, Rockville, Md.: June 2006; DOE/SC-0095.
2. Curtis S. Walseth, "Enzymatic Hydrolysis of Cellulose," Dissertation, Institute of Paper Chemistry, Appleton, Wis. 1948.
3. Bruce E. Dimick, "The Importance of the Structure of Alkali Metal Hydroxide Solutions in Decrystallizing Cellulose I," Dissertation, Institute of Paper Chemistry, Appleton, Wis. 1976.
4. R. Jeffries and J. O. Warwicker, Textile Res, J., 39, 548 (1969).
5. R. H. Atalla and R. Whitmore, "The influence of elevated temperatures of structure in the isolation of native cellulose," J. Polymer Sci. Polymer Lett. 16:601 (1978).
6. R. H. Atalla and S. C. Nagel, "Cellulose: Its regeneration in the native lattice" Science, 185:522 (1974).
7. R. H. Atalla and D. L. VanderHart, "Native cellulose: a composite of two distinct crystalline forms" Science, 223: 283 (1984).
8. R. H. Atalla and U. P. Agarwal, "Raman microprobe evidence for lignin orientation in cell walls of native woody tissue" Science, 227:636 (1985).

The invention claimed is:

1. A method of pretreating cellulose or a cellulosic material, comprising contacting the cellulose or cellulosic material with a treatment solution of an alkali in an alcohol/water co-solvent system to yield a deaggregated or decrystallized cellulose, the alkali having a concentration of >1.0 M.
2. The method of claim 1, wherein the alcohol is a primary, secondary or tertiary alcohol or a polyol.
3. The method of claim 1, wherein the alkali is NaOH, LiOH, KOH or combinations thereof.
4. The method of claim 1, wherein the alkali concentration ranges from 1.5 M to 2.0 M.
5. The method of claim 1, wherein the contacting step is for a period of between about 2 minutes to about 5 minutes.
6. The method of claim 1, further comprising washing the deaggregated or decrystallized cellulose with co-solvent to remove the alkali to a neutral pH and to stabilize the deaggregated or decrystallized cellulose in aqueous medium.
7. The method of claim 1, wherein the concentration of alkali ranges up to the threshold concentration for mercerization of the cellulose.
8. The method of claim 1, wherein the cellulose is microcrystalline cellulose and the alkali concentration is between 1 M and 2 M.
9. A method of producing sugars, comprising treating a cellulosic material with a treatment solution of an alkali in an alcohol/water co-solvent system to yield a deaggregated or decrystallized cellulosic material, the alkali having a concentration of >1.0 M; washing the cellulosic material with the co-solvent to remove the alkali, and hydrolyzing the cellulosic material to yield sugars.
10. The method of claim 9, further comprising fermenting the sugars to yield ethanol and recycling a portion of the ethanol to the co-solvent system to deaggregate or decrystallize the cellulosic material.
11. A method of producing cellulosic ethanol, comprising treating a cellulosic material with a treatment solution of an alkali in an alcohol/water co-solvent system to yield a deaggregated or decrystallized cellulosic material, the alkali having a concentration of >1.0 M; washing the cellulosic material with the co-solvent to remove the alkali; hydrolyzing the cellulosic material to yield sugars; fermenting the sugars to produce ethanol; and separating the ethanol from the fermentation mix.
12. The method of claim 11, further comprising recycling a portion of the produced ethanol to the treating step.
13. The method of claim 11, wherein a portion of the ethanol is used to produce the alcohol/water co-solvent system.
14. A method of producing cellulosic biofuels, the method comprising: treating a cellulosic material with a treatment solution of an alkali in an alcohol/water co-solvent system to yield a deaggregated or decrystallized cellulose, the alkali having a concentration of >1.0 M; washing the deaggregated or decrystallized cellulose with the co-solvent to remove the alkali; and catalytically reforming the deaggregated or decrystallized cellulose into hydrocarbons or biofuels.
15. A method of producing cellulosic biofuels, the method comprising: treating a cellulosic material with a treatment solution of an alkali in an alcohol/water co-solvent system to yield a deaggregated or decrystallized cellulose, the alkali having a concentration of >1.0 M; washing the deaggregated or decrystallized cellulose to remove the alkali; hydrolyzing the deaggregated or decrystallized cellulose to glucose and cello-oligodextrins; and catalytically reforming the glucose and cello-oligodextrins into hydrocarbons.

16. A method of producing biofuels, comprising: a) hydrolyzing a cellulosic material to form glucose and a residual cellulose; b) treating the residual cellulose with a treatment solution of an alkali in an alcohol/water co-solvent system to yield a deaggregated or decrystallized cellulose, the alkali having a concentration of >1.0 M; c) washing the deaggregated or decrystallized cellulose to remove the alkali; and d) hydrolyzing the deaggregated or decrystallized cellulose to glucose and cello-oligodextrins.

17. The method of claim 16, further comprising catalytically reforming the glucose and cello-dextrins to hydrocarbons.

* * * * *

UNITED STATES PATENT AND TRADEMARK OFFICE
CERTIFICATE OF CORRECTION

PATENT NO. : 8,617,851 B2  Page 1 of 1
APPLICATION NO. : 12/935447
DATED : December 31, 2013
INVENTOR(S) : Rajai H. Atalla It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 137 days.

Signed and Sealed this
Twenty-second Day of September, 2015

Michelle K. Lee
*Director of the United States Patent and Trademark Office*